US 6,642,720 B2

(12) United States Patent
Maylotte et al.

(10) Patent No.: US 6,642,720 B2
(45) Date of Patent: Nov. 4, 2003

(54) WIRELESS SENSOR ASSEMBLY FOR CIRCUMFERENTIAL MONITORING OF GAS STREAM PROPERTIES

(75) Inventors: Donald Herbert Maylotte, Schenectady, NY (US); James Peter DeLancey, Corinth, NY (US)

(73) Assignee: General Electric Company, Niskayuna, NY (US)

( * ) Notice: Subject to any disclaimer, the term of this patent is extended or adjusted under 35 U.S.C. 154(b) by 119 days.

(21) Appl. No.: 09/682,130

(22) Filed: Jul. 25, 2001

(65) Prior Publication Data

US 2003/0020480 A1 Jan. 30, 2003

(51) Int. Cl.[7] .......................... G01R 27/26; G01N 7/00; G08C 19/10; F02D 41/00
(52) U.S. Cl. ...................... 324/464; 324/686; 73/23.31; 340/870.17; 123/676
(58) Field of Search ................................. 324/464, 658, 324/519, 686; 73/23.31, 31.05, 28.01, 335.04; 416/96 R; 123/676; 340/870.17, 870.31, 870.37

(56) References Cited

U.S. PATENT DOCUMENTS

| | | | | | |
|---|---|---|---|---|---|
| 4,761,101 A | * | 8/1988 | Zettl | .............................. | 408/6 |
| 5,231,359 A | * | 7/1993 | Masuda et al. | ............. | 324/675 |
| 5,381,660 A | * | 1/1995 | Loving et al. | ................ | 60/303 |
| 5,657,625 A | | 8/1997 | Koga et al. | | |
| 5,756,879 A | * | 5/1998 | Yamagishi et al. | ........ | 73/28.01 |
| 5,880,354 A | * | 3/1999 | Newman et al. | ........... | 73/25.01 |
| 5,927,648 A | | 7/1999 | Woodland | | |
| 5,979,220 A | * | 11/1999 | Zombo et al. | ............... | 73/23.2 |
| 6,319,484 B1 | * | 11/2001 | Shore et al. | ............. | 423/245.1 |

* cited by examiner

*Primary Examiner*—Anjan K. Deb
(74) *Attorney, Agent, or Firm*—Patrick K. Patnode; Christian G. Cabou

(57) ABSTRACT

A wireless sensor assembly for circumferential monitoring of gas stream properties comprises a drive system attachable to a hot gas path housing. A rake is movably coupled to the drive system for unrestricted circumferential movement. At least one RF sensor is disposed on the rake for generating a signal responsive to the gas stream properties. Circuitry is provided for remotely powering the at least one RF sensor and for remotely detecting the signal.

38 Claims, 2 Drawing Sheets

WIRELESS SENSOR ASSEMBLY FOR CIRCUMFERENTIAL MONITORING OF GAS STREAM PROPERTIES

BACKGROUND OF INVENTION

The present invention is related to a sensor assembly for determining selected properties of a gas. More particularly, the present invention relates to a wireless sensor assembly for measuring selected properties of a gas stream passing through a gas path housing.

The health and performance of structures such as turbine assemblies, blast furnaces, boilers, and the like can often be monitored by tracking a physical property, such as temperature, of a gas stream passing through such a structure. By monitoring levels and variations of such properties, structures such as those mentioned above may be operated at peak efficiency. In addition, such monitoring may serve as a diagnostic tool for identifying events within such structures that may lead to a degradation of performance.

For example, in a turbine engine, such as those widely used for power generation or aircraft propulsion, air enters the combustor section where it is combined with a fuel, such as natural gas or jet fuel, and burned continuously within a plurality of combustor cans. In most turbine designs, the combustor section typically includes about 14 combustors. The hot, high pressure air exiting the combustor section is then expanded before exiting the turbine engine through the exhaust section. As a result of the combustion of gases within the combustor cans, the gases passing through the exhaust section exhibit a distinctive temperature profile roughly corresponding to the annular distribution of combustor cans within the combustor section. Thus, an event that causes a combustor can to cease functioning will result in a corresponding change in the temperature profile.

Because the turbine engine typically contains about 14 combustor cans, multiple temperature probes are required to provide sufficient resolution to accurately monitor any changes in the temperature profile. The positioning of multiple temperature probes in the exhaust system is undesirable, due to the disruption of gas flow by such an array and the resulting loss of turbine efficiency. The use of multiple temperature probes is also impractical, due to the complex hard-wiring that such an array would require.

Thus, there is a need for a sensor system that is capable of monitoring and profiling the properties of a gas stream passing through a hot gas path housing, such as a turbine engine or assembly

SUMMARY OF INVENTION

A wireless sensor assembly for circumferential monitoring of gas stream properties comprises a drive system attachable to a hot gas path housing. A rake is movably coupled to the drive system for unrestricted circumferential movement. At least one RF sensor is disposed on the rake for generating a signal responsive to the gas stream properties. Circuitry is provided for remotely powering the at least one RF sensor and for remotely detecting the signal.

DETAILED DESCRIPTION

Figure 1:
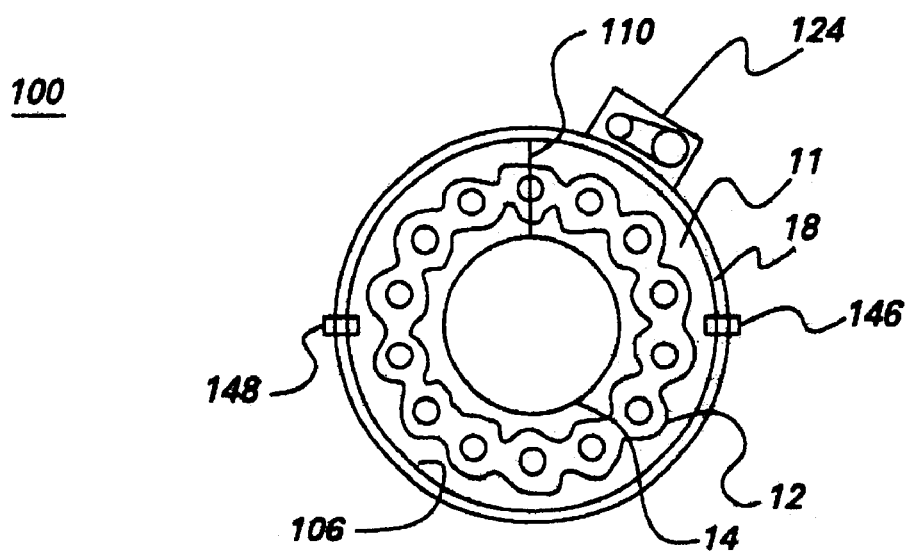
FIG. 1 is an annular end view of an exhaust section of a turbine system.

In the following description, like reference characters designate like or corresponding parts throughout the several views shown in the figures. It is also understood that terms such as "top," "bottom," "outward," "inward," and the like are words of convenience and are not to be construed as limiting terms.

Figure 3:
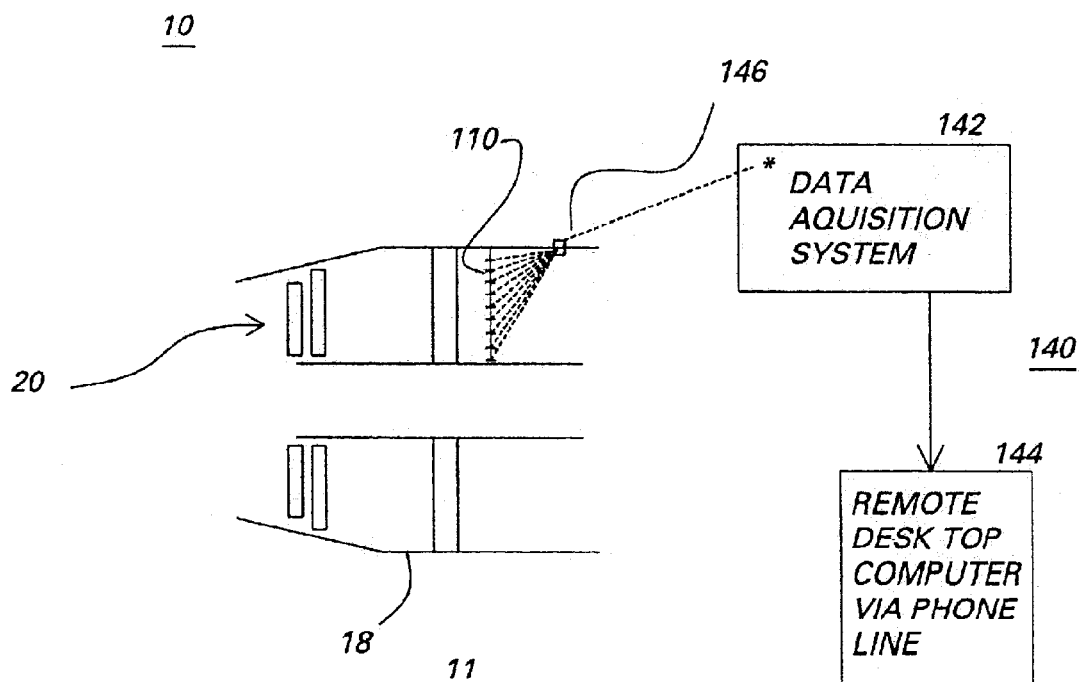
FIG. 3 is a schematic side view showing location of the sensor probe of the present invention within the exhaust section of a turbine system.

Referring to the drawings in general and to FIG. 1 in particular, it will be understood that the illustrations are for the purpose of describing a preferred embodiment of the invention and are not intended to limit the invention thereto. FIG. 1 is an annular end view of an exhaust section 11 of a turbine engine 10. (FIG. 3) The turbine engine 10 may either be a land-based turbine, such as those widely used for power generation, or an aircraft engine. Air enters the inlet of the turbine engine 10, is first compressed, and then enters the combustor section where it is combined with a fuel, such as natural gas or jet fuel, and burned continuously within a plurality of combustor cans. In most turbine designs, the combustor section typically includes about 14 combustors. The hot, high pressure air exiting the combustor section is then expanded through a turbine, where energy is extracted to power the compressor, before exiting the turbine engine 10 through the exhaust section 11. (FIG. 1)

As a result of the combustion of gases within the combustor cans, the gases passing through the exhaust section 11 exhibit a distinctive temperature profile 12, both radially and circumferentially, within the exhaust section 11. The temperature profile 12 roughly corresponds to the annular distribution of combustor cans within the combustor section of the turbine engine 10. (FIG. 3) Thus, an event that causes a combustor can to cease functioning or to malfunction will result in a corresponding change in the temperature profile 12. (FIG. 1)

Because turbine engine 10 typically contains about 14 combustor cans, multiple temperature probes are required to provide sufficient resolution to accurately monitor any changes in the temperature profile 12. The positioning of multiple temperature probes in the exhaust system is undesirable, due to the disruption of gas flow by such an array and the resulting loss of turbine efficiency. The use of multiple temperature probes is also impractical, due to the complex hard-wiring that such an array would require.

Referring to FIG. 1, the wireless sensor assembly 100 of the present invention, shown in a cross-sectional schematic view, provides for the circumferential monitoring of the properties of gases within a hot gas path 20 (FIG. 3) contained within a hot gas housing, such as, but not limited to, the exhaust section 11 of a turbine engine 10. The wireless sensor assembly 100 (FIGS. 1,2) includes a single movable sensor probe or "rake" 110 having at least one radio frequency (RF) sensor 112 contained either within the rake 110 or, alternatively, on the surface of the rake 110. The wireless sensor assembly 100 also includes circuitry 140 adapted to remotely power the RF sensor 112 and to detect signals generated by the RF sensors 112.

RF sensor 112 is capable of both receiving a RF signal, and generating a signal that is responsive to the physical properties of the gases within the hot gas path 20. Preferably, a plurality of RF sensors 112 are contained within the rake 110. The rake 110 is coupled to a drive system 120 that is attached to the hot gas housing which, in one embodiment, is outer wall 18 of the exhaust section 11. The drive system 120 enables the rake 110 to move about the circumference of the annular space within the exhaust section 11.

The rake 110 projects radially into the hot gas path 20 to expose the RF sensors 112 to the hot gas stream. Whereas FIG. 1 shows the rake 110 of the present invention movably installed on the inside surface of the outer wall 18 and extending radially inward from the outer wall 18, the rake 110 may alternatively be movably installed on the inner wall 14 of the annular exhaust section 11. The RF sensors 112 are capable of transmitting and receiving radio signals from an antenna 146 mounted on the outer wall 18 of the turbine engine 10.

Depending on the nature and structure of the hot gas housing and combustion source, components of the wireless sensor assembly 100, particularly portions of the drive system 120, rake 110, and RF sensors 112, may be exposed to high temperature gases. In a turbine engine 10, for example, the rake 110 may be located either upstream, close to the power extraction section of the turbine engine 10, or downstream, toward the outlet of the exhaust section 12. Thus, the wireless sensor assembly 100 is preferably capable of operating at temperatures of at least about 200° C.

Drive system 120 includes a circular drive path mechanism 122. The circular drive path mechanism 122 extends around the entire circumference of an inside surface the outer wall 18. The rake 110 is coupled to the circular drive path mechanism 122 by a carriage mount (not shown), such as those widely known in the art, so as to travel circumferentially around the hot gas path housing, thereby permitting the RF sensors 112 to be located either within or on the rake 110 in order to measure the desired properties within the hot gas path 20. The carriage mount positions the rake 110 such that the rake 110 is substantially normal to the outer wall 18, and extends radially inward therefrom. Alternatively, when the rake 110 is movably installed on the inner wall 14 of the annular exhaust section 11, the carriage mount positions the rake such that the rake 110 extends radially outward from the, and substantially normal to, the inner wall 14.

A prime mover 124 coupled to the circular drive path mechanism 122 causes the circular drive path mechanism 122 to move and the rake 110 to travel along the circumferential path. The prime mover 124 is typically a drive motor, such as those known in the art, which is disposed outside the outer wall 18. Prime mover 124 may be coupled to the drive mechanism 122 by a drive shaft and gear, chain drive, belt drive, or the like.

The circular drive path mechanism 122 may be a chain, cable, or the like, and is preferably made of stainless steel. As previously mentioned, components of the wireless sensor assembly 100, particularly portions of the drive system 120 may be exposed to high temperature gases during operation. Therefore, the circular drive path mechanism 122 and carriage mount are preferably capable of operating at greater than about 1400° F. The circular drive path mechanism 122 may be encased in a raceway 126 to maintain the circular drive path mechanism 122 and rake 110 on a circumferential track. The raceway 126 may be incorporated into a portion of the outer wall 18, or may be insertable between two adjacent portions of the outer wall 18.

Many of the events, such as the failure of a combustor can, occurring within the turbine engine are not self-repairing. Thus, the indicia of such events, such as a change in the temperature profile 12, persist for significant periods of time thereafter. Therefore, it is not necessary for the wireless sensor assembly 100 of the present invention to instantaneously detect such events. The rake 110 is conveyed around a circumferential track by the drive system 120 at a rate such that the RF sensors 112 contained in the rake 110 sweep substantially the entire cross-section of the hot gas path 20 in a reasonable time period; i.e., a period that allows sufficient time for the RF sensors 112 to detect a predetermined property. Preferably, the drive system 120 moves the rake 110 at a rate of between about 10° per minute to about 360° per minute. Thus, a sweep of substantially the entire cross-section of the hot gas path 20 by the RF sensors 112 contained in the rake 110 would be made every 1 to 36 minutes. More preferably, the drive system 120 moves the rake 110 at a rate of between about 48° per minute to about 90° per minute, thus sweeping substantially the entire cross-section of the hot gas path 20 by the RF sensors 112 contained in the rake 110 every 7.5 to 4 minutes.

The drive mechanism 120 is capable of conveying the rake 110 circumferentially around the hot gas path housing in either a clockwise or counterclockwise direction. Moreover, in one embodiment, drive mechanism 120 allows the direction of travel of rake 110 to be reversed during operation of the wireless sensor assembly 100. The wireless sensor assembly 100 may also include a position control mechanism, such as a timer, micrometer, or the like, for determining the location of the rake 110 in the hot gas path 20 at any given time.

Figure 2:
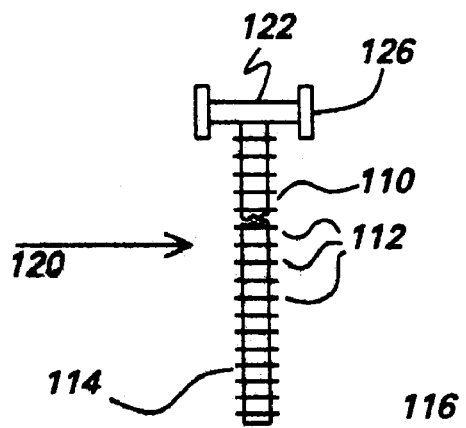
FIG. 2 is a schematic side view of the sensor probe of the present invention.

Rake 110 may be a single rod structure, a bifurcated rod, an angled rod, or the like. To withstand the temperatures of gases within the hot gas path, the rake 110 is preferably made from an alloy, such as, but not limited to, Hasteloy, nickel-based alloys, cobalt-based alloys, and the like. In one embodiment, rake 110 has an internal cavity that may accommodate at least one RF sensor 112. FIG. 2 shows a rake 110, having a plurality of RF sensors 112, extending into the hot gas path 20. The length of rake 110 depends on the dimensions of the hot gas path 20.

RF sensor 112 is selected for its sensitivity to a particular property, such as temperature, of gases within hot gas path 20. Alternatively, RF sensor 112 may be sensitive to concentrations of particulate matter or to different chemical species in hot gas path 20. Among the species that may be detected or monitored by RF sensor 112 are nitrous oxides (NOx), salts, oxygen, carbon monoxide, carbon dioxide, and the like. Rake 110 may include a plurality of RF sensors 112, each of which is sensitive to a different property or component present within the hot gas path.

Figure 4:
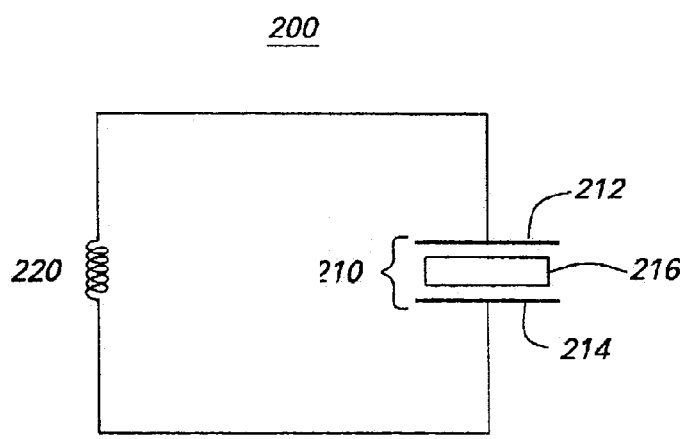
FIG. 4 is a schematic diagram of a LC circuit used in the RF sensor of the present invention.

In one embodiment, RF sensor 112 comprises a LC circuit 200, shown in FIG. 4, wherein LCR circuit 200 comprises an inductor 220 and capacitor 210. The resistance may either be a separate component or the implicit resistance of the other components. Capacitor 210 comprises two plates 212, 214 and a dielectric material 216 disposed therebetween. RF sensor 112 is oriented such that capacitor 210 with dielectric material 216 disposed between plates 212, 214 is oriented facing hot gas path 20. When irradiated with electromagnetic energy of a predetermined frequency, such as radio waves, LC circuit 200 resonates at a characteristic frequency, which is dependent in part upon the dielectric constant of dielectric material 216. Preferably, LC circuit 200 of RF sensor 112 is responsive to a frequency of at least about 1 MHz and, more preferably, to a frequency in the range of between about 200 MHz and about 600 MHz.

In one embodiment, RF sensor 112 comprising LC circuit 200 is capable of detecting the temperature of the hot gas path 20. Preferably, RF sensor 112 is capable of sensing temperatures of at least about 900° F. In the present invention, the dielectric constant of dielectric material 212 varies as a function of temperature. Thus, the resonance frequency of LC circuit 200 of RF sensor 110 is indicative of the temperature of gases within hot gas path 20.

The number of RF sensors 112 disposed within rake 110 is limited in part by the size of each RF sensor 112. An RF sensor 112 comprising an LC circuit 200 has dimensions of about 0.5 inch by about 0.5 inch. Thus, up to two RF sensors 112 per inch of rake length may be disposed in rake 110. In addition, the number of RF sensors 112 disposed within rake 110 also depends upon the density of information desired for a given property, such as temperature, the ability of the wireless sensor assembly 100 to provide sufficient power to the RF sensors 112, and the ability of the wireless sensor assembly 100 to distinguish between the resonant frequencies of each RF sensor 112.

Rake 110 has a length that allows the wireless sensor assembly 100 to detect properties at a desired point within the hot gas path 20. The length of rake 110 depends in part upon the location of the rake 110 within a hot gas housing, such as the exhaust section 11 of turbine engine 10. Thus, rake 110 may have a length of between about 6 inches and about 48 inches. Preferably, rake 110 is between about 24 inches and about 36 inches in length.

The wireless sensor assembly 100 also includes circuitry 140, which is capable of remotely powering at least one RF sensor 112 and receiving a signal generated by RF sensor 112. Circuitry 140 is typically a pulsed circuit, and, in one embodiment, includes an RF power source, a microprocessor, and an RF detector. In order to determine which RF sensor 112 is transmitting a signal, the RF detector, in one embodiment, is capable of discriminating among the signals generated by multiple RF sensors 112. Circuitry 140 may also include data acquisition system 142 for collecting, storing, and processing data transmitted from the RF sensors 112. Data acquisition system 142 may also be capable of transmitting data to a remote control center 144, which is capable of monitoring the wireless sensor assembly 100 and modifying operational parameters of the wireless sensor assembly 100. Transmission of data from the data acquisition system 142 to remote control center 144 may take place by means, such as wireless transmission, telephone connection, or the like, that are well known in the art.

Circuitry 140 includes at least one antenna 146 disposed on the inner surface of the outer wall 18 of the hot gas path housing for generating a signal, preferably a pulsed signal, that powers RF sensors 112 and receiving signals transmitted therefrom. Antenna 146 may be capable of generating a signal having a bandwidth to cover the range of resonant frequencies of all of the RF sensors 112. Alternatively, antenna 146 generates a signal having a bandwidth corresponding to a resonant frequency of a specific RF sensor 112. In one embodiment of the present invention, two antennas 146, 148, are disposed on the inner surface of the outer wall 18, wherein antennas 146 and 148 are preferably spaced 180° apart, as shown in FIG. 1.

In operation, drive system 120 moves rake 110 circumferentially about the hot gas path 20 at a predetermined rate. At least one RF sensor 112 is disposed within rake 110 such that RF sensor 112 is responsive to the properties of hot gas path 20. Antenna 146 provides power to RF sensor 112. In response to the power provided by antenna 146, RF sensor 112 then generates a signal having a frequency that is proportional to the properties of hot gas path 20. The signal from RF sensor 112 is received by circuitry 140, which includes an RF detector. The signal is collected, stored, and analyzed by data acquisition system 142. Data acquisition system 142 may then transmit data to remote control center 144, which is capable of monitoring the wireless sensor assembly 100 and modifying operational parameters of the wireless sensor assembly 100.

While various embodiments are described herein, it will be apparent from the specification that various combinations of elements, variations, or improvements thereon may be made by those skilled in the art, and are thus within the scope of the invention. For example, the installation of the wireless sensor assembly of the present invention is not limited to locations within the exhaust section of a turbine engine. The wireless sensor assembly may also be adapted for use in other sections of a turbine assembly, such as the combustor, where it is may be desirable to monitor selected properties of the hot gas path. In addition, the wireless sensor assembly may be adapted to other structures, such as boilers, blast furnaces, and the like, in which it is desirable to monitor selected properties of a hot gas path.

What is claimed is:

1. A wireless sensor assembly for circumferential monitoring of gas stream properties comprising:
   a drive system attachable to a hot gas path housing;
   a rake movably coupled to said drive system for unrestricted circumferential movement;
   at least one RF sensor disposed on said rake for generating a signal responsive to said gas stream properties; and
   circuitry for remotely powering said at least one RF sensor and for remotely detecting said signal.

2. A wireless sensor assembly in accordance with claim 1, wherein said wireless sensor assembly is capable of operating at temperatures of greater than about 200° C.

3. A wireless sensor assembly in accordance with claim 2, wherein said circular drive path mechanism is at least one of a chain or a cable.

4. A wireless sensor assembly in accordance with claim 3, wherein said chain or cable is capable of operating at 1400° F. (760_° C.) or greater.

5. A wireless sensor assembly in accordance with claim 3, wherein said chain is made of stainless steel.

6. A wireless sensor assembly in accordance with claim 1, wherein said drive system is a circular drive path mechanism.

7. A wireless sensor assembly in accordance with claim 6, wherein said circular drive path mechanism is a circumferential channel.

8. A wireless sensor assembly in accordance with claim 1, further comprising a prime mover disposed outside said hot gas path and coupled to said drive system for circumferential movement thereof.

9. A wireless sensor assembly in accordance with claim 1, wherein said drive system moves in the range between about 10_°/minute to about 360_°/minute.

10. A wireless sensor assembly in accordance with claim 1, wherein said drive system moves in the range between about 48_°/minute to about 90_°/minute.

11. A wireless sensor assembly in accordance with claim 1, further including a position detection control mechanism.

12. A wireless sensor assembly in accordance with claim 1, wherein said position detection control mechanism is a timer.

13. A wireless sensor assembly in accordance with claim 1, wherein said rake is a rod.

14. A wireless sensor assembly in accordance with claim 1, wherein said rake is a bifurcated rod.

15. A wireless sensor assembly in accordance with claim 1, wherein said rake is an angled rod.

16. A wireless sensor assembly in accordance with claim 1, wherein said rake is made of a material selected from the group consisting of Hastelloy, a nickel-based alloy and a cobalt-based alloy.

17. A wireless sensor assembly in accordance with claim 1, wherein said drive system further comprises a carriage mount for coupling said rake to said drive system.

18. A wireless sensor assembly in accordance with claim 17, wherein said carriage mount is capable of operating at temperatures greater than 1400° F.

19. A wireless sensor assembly in accordance with claim 17, wherein said carriage mount positions said rake substantially normal to said hot gas path housing.

20. A wireless sensor assembly in accordance with claim 1, wherein said RF sensor comprises an LC circuit including an induction coil and a capacitor having a dielectric material, which dielectric material has a dielectric constant that is a function of temperature.

21. A wireless sensor assembly in accordance with claim 20, wherein said dielectric is capable of sensing temperatures of at least 900° F. (482_°C.).

22. A wireless sensor assembly in accordance with claim 21, wherein said ceramic base is selected from the group consisting of alumina and zirconia.

23. A wireless sensor assembly in accordance with claim 1, wherein said RF sensor is responsive to a frequency of at least 1 MHz.

24. A wireless sensor assembly in accordance with claim 1, wherein said RF sensor is responsive to a frequency in the range between about 200 MHz to about 600 MHz.

25. A wireless sensor in accordance with claim 1, wherein said RF sensor is sensitive to a property selected from the group consisting of temperature, NOx concentration, salt concentration, oxygen concentration, carbon monoxide concentration, carbon dioxide concentration and particulate concentration.

26. A wireless sensor assembly in accordance with claim 1, wherein said RF sensor has a ceramic base.

27. A wireless sensor assembly in accordance with claim 1, wherein said circuitry is a pulsed circuit.

28. A wireless sensor assembly in accordance with claim 1, wherein said circuitry includes a power source, a microprocessor and an RF detector.

29. A wireless sensor assembly in accordance with claim 28, wherein said circuitry further includes a data acquisition device.

30. A wireless sensor assembly in accordance with claim 29, wherein said circuitry includes at least one antenna disposed upon said housing.

31. A wireless sensor assembly in accordance with claim 30, wherein said at least one antenna is two antennas spaced apart by 180°.

32. A wireless sensor assembly in accordance with claim 31, wherein said at least one antenna generates a signal to power said RF sensor.

33. A wireless sensor assembly in accordance with claim 31, wherein said antenna generates a signal having a bandwidth to cover the range frequencies for each respective RF sensor.

34. A wireless sensor assembly in accordance with claim 31, wherein said antenna generates a signal having a bandwidth with a specific frequency related to a specific RF sensor.

35. A wireless sensor assembly in accordance with claim 31, wherein said antenna sends pulses to said at least one RF sensor.

36. A wireless sensor assembly in accordance with claim 31, wherein said RF detector can discriminate between frequencies to determine which RF sensor is detected.

37. A wireless sensor for circumferential monitoring of gas stream properties within a hot gas path housing, said sensor comprising:

an RF sensor for generating a signal responsive to said gas stream temperature said RF sensor including an induction coil and a capacitor, said capacitor having a dielectric material, which dielectric material has a dielectric constant that is proportional to temperature;

an antenna for generating signals to power said RF sensor;

an RF detector for detecting the signal generated from the RF sensor; and a microprocessor coupled to said RF detector to correlate the detected signal with the temperature of said gas stream.

38. A method of monitoring gas stream properties within a hot gas path comprising the steps of:

positioning an RF sensor sensitive to a respective gas stream property within said hot gas path for generating a signal responsive to said property;

rotating said RF sensor about said hot gas path housing;

remotely powering said RF sensor;

remotely monitoring said generated signals; and detecting said generating signals.

* * * * *